(12) United States Patent
Li et al.

(10) Patent No.: US 6,303,136 B1
(45) Date of Patent: Oct. 16, 2001

(54) CELLS OR TISSUE ATTACHED TO A NON-DEGRADABLE FILAMENTOUS MATRIX ENCAPSULATED BY A SEMI-PERMEABLE MEMBRANE

(75) Inventors: Rebecca Li, Needham, MA (US); David Rein, Providence, RI (US)

(73) Assignee: Neurotech S.A., Evry (FR)

( * ) Notice: Subject to any disclaimer, the term of this patent is extended or adjusted under 35 U.S.C. 154(b) by 0 days.

(21) Appl. No.: 09/289,999

(22) Filed: Apr. 12, 1999

Related U.S. Application Data
(60) Provisional application No. 60/081,512, filed on Apr. 13, 1998.

(51) Int. Cl.[7] ............. A61F 2/00; A01N 63/00; C12N 11/02; C12N 5/06; C12N 5/08
(52) U.S. Cl. ............. 424/424; 424/415; 424/93.7; 435/176; 435/177; 435/178; 435/179; 435/180; 435/182; 435/382; 435/395; 435/398; 435/402
(58) Field of Search ................. 424/93.7, 423, 424/424, 451; 435/174, 177, 180, 395, 396, 398, 399, 401, 402, 176, 178, 179, 182, 382

(56) References Cited

U.S. PATENT DOCUMENTS

| | | | |
|---|---|---|---|
| 4,686,098 | 8/1987 | Kopchick et al. | 424/424 |
| 4,968,733 | 11/1990 | Muller et al. | 521/64 |
| 4,976,859 | 12/1990 | Wechs | 210/500.23 |
| 5,158,881 | 10/1992 | Aebischer et al. | 435/182 |
| 5,284,761 | 2/1994 | Aebischer et al. | 435/182 |
| 5,512,600 | 4/1996 | Mikos et al. | 521/61 |
| 5,653,975 | 8/1997 | Baetge et al. | 424/93.1 |
| 5,786,216 | * 7/1998 | Dionne et al. | 435/402 |
| 5,795,790 | 8/1998 | Schinstine et al. | 435/382 |
| 5,800,828 | 9/1998 | Dionne et al. | 435/422 |
| 5,980,889 | * 11/1999 | Butler et al. | 424/93.7 |
| 6,054,142 | * 4/2000 | Li et al. | 424/426 |

FOREIGN PATENT DOCUMENTS

| | | |
|---|---|---|
| 1422854 | 1/1976 | (GB) . |
| 91/10425 | 7/1991 | (WO) . |
| 92/19195 | 11/1992 | (WO) . |
| 95/05452 | 2/1995 | (WO) . |
| 95/28166 | 10/1995 | (WO) . |
| 96/40871 | 12/1996 | (WO) . |
| 97/10807 | 3/1997 | (WO) . |
| 98/05304 | 2/1998 | (WO) . |

OTHER PUBLICATIONS

Shoichet & Rein, In vivo biostability of a polymeric hollow fibre membrane for cell encapsulation. 17 Biomaterials 285–290 (1996).

* cited by examiner

*Primary Examiner*—David M. Naff
(74) *Attorney, Agent, or Firm*—Mintz, Levin, Cohn, Ferris, Clovsky and Popeo, P.C.; Ivor R. Elrifi; Christina V. Karnakis

(57) ABSTRACT

A device is prepared having cells or tissue attached to a non-degradable filamentous matrix surrounded by a semi-permeable membrane. The matrix is preferably formed of a plurality of monofilaments twisted into a yarn or woven into a mesh, and can be in the form of a cylinder. When implanting the device, the semi-permeable membrane is preferably immunolsolatory, and the cells or tissue may produce a biologically active molecule to provide therapy. To enhance cell or tissue adhesion, the matrix is coated with extracellular matrix molecules or treated to provide a surface charge. The device can be made by inserting the matrix into a capsule formed of the semi-permeable membrane, distributing the cells or tissue on the matrix through an opening of the capsule, and sealing the opening of the capsule.

12 Claims, 7 Drawing Sheets

CELLS OR TISSUE ATTACHED TO A NON-DEGRADABLE FILAMENTOUS MATRIX ENCAPSULATED BY A SEMI-PERMEABLE MEMBRANE

RELATED U.S. APPLICATION

This application claims priority under 35 U.S.C. §119(e) to U.S. Provisional Patent Application No. 60/081,512, filed Apr. 13, 1998.

FIELD OF THE INVENTION

This invention relates generally to cell encapsulation devices, and more particularly to devices for cell screening and implantation into a mammalian host.

BACKGROUND OF THE INVENTION

In encapsulated cell therapy, xenogenic or allogenic cells are isolated from the host's immune system by being surrounded in a semi-permeable membrane prior to implantation within the host. The semi-permeable membrane is relatively impermeable to large molecules, such as components of the host's immune system, but is permeable to small molecules. Thus, the semi-permeable membrane allows the implanted cells to receive nutrients necessary for viability and allows metabolic waste to be removed. The membrane also allows therapeutic molecules produced by the implanted cells to diffuse to host cells. For example, endogenous proteins or those cloned into the cell are delivered to the host. The use of an immuno-protective, semi-permeable membrane now allows transplantation of encapsulated cells from one species into a host from a different species without the risk of immune rejection or use of immunosuppressive drugs. Applications of encapsulated cell therapy include, for example, treatment for diabetes, haemophilia, anemia, β-thalassemia, Parkinson's disease, and amyotropic lateral sclerosis.

The use of biologically compatible polymeric materials in construction of an encapsulation device is critical to a successful cell encapsulation therapy. Important components of the encapsulation device include the surrounding semi-permeable membrane and the internal cell-supporting matrix or scaffold. The scaffold defines the microenvironment for the encapsulated cells and keeps the cells well distributed within the intracapsular compartment. The optimal internal scaffold for a particular cell encapsulation device is highly dependent on the cell type. For example, while adherent cells often prefer a solid surface on which to lie, suspension cells may prefer a hydrophilic lightly cross-linked hydrogel as a matrix material.

In the absence of a scaffold, adherent cells aggregate to form clusters. When the clusters grow too large, they typically develop a central necrotic core. Dying cells accumulate around the core and, upon lysing, release factors detrimental to the health of neighboring cells. The lysed cell fragments are also transported to the host environment, there eliciting an antigenic response.

Several types of prior art devices have attempted to solve these problems, meeting with mixed results. For example, the prior art includes the use of bonded fiber structures for cell implantation (U.S. Pat. No. 5,512,600) and the use of biodegradable polymers as scaffolds for organ regeneration such as, for example, liver, pancreas, and cartilage. The use of biodegradable polymers for use as scaffolds in organ regeneration is reviewed by Cima et al., BIOTECH. BIOENG. 38: 145–58 (1991). In these prior art works, biodegradable fiber tassels and fiber-based felts (i.e., non-woven materials) were used as scaffolds for transplanted cells. One drawback to the use of biodegradable polymers, particularly polymers of poly(lactic acid) PLA, poly(lactic-coglycolic acid) PLGA, poly(glycolic acid) PGA, and their equivalents, is that upon degradation, they release lactic and/or glycolic acid, which are toxic to surrounding tissue. As the polymers degrade, they break down to first low molecular weight oligomers and then to the acids, causing a rapid increase in acid released into the surrounding tissue. This rise in acid concentration in vivo in the local environment of the implant can induce an inflammatory response or tissue necrosis.

Foam scaffolds have also been used in the art to provide surfaces onto which transplanted cells may adhere. Foam scaffolds, however, have random flat surfaces and do not provide a linear template for reorganization. Some cell types prefer such a template for organization into physiological three-dimensional orientation.

Prior art also includes woven mesh tubes used as vascular grafts. Although cells may be seeded onto these woven tubes for improved biocompatibility, these tubes function primarily as vascular conduits and not cell scaffolds.

Thus, a need exists in the art for a non-degradable scaffold or framework system to provide an ordered linear environment for cells which prefer such an environment to grow and proliferate within cell encapsulation devices.

SUMMARY OF THE INVENTION

The invention provides a cell encapsulation device for growing, maintaining, proliferating and/or differentiating viable cells. The device has (1) an internal filamentous cell-supporting matrix or scaffolding comprising a plurality of filaments, preferably spun into one or more yarns, or alternatively woven into one or more mesh components, and (2) an encapsulating permselective membrane. Cells are seeded onto the yarn or mesh scaffolding, which is encapsulated by the permselective membrane. The cell matrix, or scaffold, in the device of the invention advantageously provides cells with a template for cellular organization in a three-dimensional orientation resembling their typical physiological shape. The cell matrix is particularly useful for the use of adherent cells in encapsulated cell therapy.

In one embodiment, the filamentous cell-supporting matrix, or scaffold, is made from any substantially non-degradable, biocompatible material. For example, the material can be acrylic, polyester, polyethylene, polypropylene, polyacetonitrile, polyethylene terephthalate, nylon, polyamides, polyurethanes, polybutester, silk, cotton, chitin, carbon, or biocompatible metals.

In a preferred embodiment, the core scaffold contains a plurality of monofilaments. In one example, the monofilaments are twisted into yarn. In another example, the plurality of monofilaments or the yarn is woven into mesh. In still other examples, the mesh is configured as a hollow cylinder, or tube, or woven into a solid cylinder, or cord.

In another embodiment, the scaffolding is coated with extracellular matrix (ECM) molecules. Suitable ECM molecules include, for example, collagen, laminin, and fibronectin. The surface of the scaffolding may also be modified by treating with plasma irradiation to enhance cell adhesion to the scaffolding.

The present invention provides several advantages over the prior art. Meshes and yarns have configurations that provide an ordered environment for cell types that may prefer such a template for reorganization into their physiological three-dimensional orientation. Also, the fibers used in the invention are substantially non-degradable and so do not release by-products into the host. Moreover, the yarn and mesh matrices of the invention have the following advantages over prior art hydrogel matrices: (1) they provide considerable added elasticity, compressive and tensile strength to hollow fiber membrane-based devices if attached at both ends of the device; (2) they provide a physical surface onto which extracellular matrix molecules may be attached; (3) they allow adherent cell types to attach and lay down their own extracellular matrix material; (4) they can be treated with a surface charge to enhance cell adhesion to the surface; (5) the yarn or mesh matrix can keep cells distributed more evenly both longitudinally and transversely and thus prevent cell clumping which leads to subsequent necrotic core formation; (6) they offer greater biological stability than hydrogel materials and have a long history of implant use as vascular grafts and suture materials; and (7) they allow certain cell types to orient in the direction parallel to the filaments or allow cells to bridge between filaments and form an ordered orientation.

In embodiments where the mesh woven tubes or yarns are affixed at both ends of the device, the overall device tensile strength, compressive strength, and kink resistance is also greatly improved. As a result, this insert of a mesh woven tube or yarns provides a method of inner support to strengthen the hollow fiber membrane device.

DETAILED DESCRIPTION OF THE INVENTION

Figure 1:
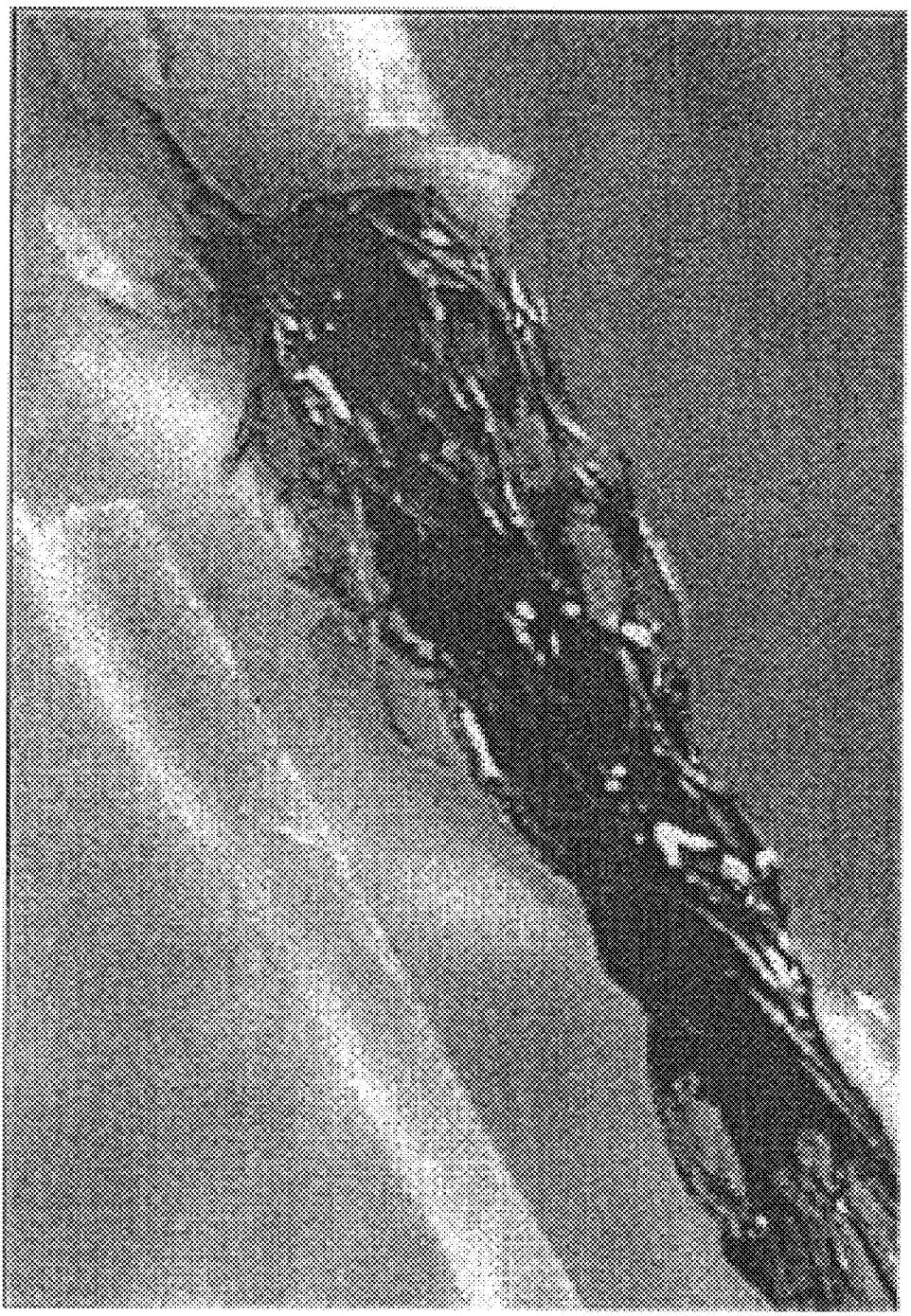
FIG. 1 is a depiction of PET yarn woven into a braid and stained with MTT black for viable cells.

This invention provides devices for cell encapsulation therapy. The devices are composed of (1) a plurality of non-degradable filaments (which may be twisted into yarns or woven into a mesh tube), that permits cell attachment; and (2) a surrounding permselective membrane jacket configured as a flat sheet or as a hollow tube. In certain embodiments, living cells are seeded and maintained within the device.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

Filaments

The filaments used to form the yarn or mesh internal scaffold are formed of any suitable biocompatible, substantially non-degradable material. Materials useful in forming yarns or woven meshes include any biocompatible polymers that are able to be formed into fibers such as, for example, acrylic, polyester, polyethylene, polypropylene, polyacrylonitrile, polyethylene terephthalate, nylon, polyamides, polyurethanes, polybutester, or natural fibers such as cotton, silk, chitin or carbon. Any suitable thermoplastic polymer, thermoplastic elastomer, or other synthetic or natural material with fiber-forming properties may be inserted into a pre-fabricated hollow fiber membrane or a hollow cylinder formed from a flat membrane sheet. For example, silk, PET or nylon filaments used for suture materials or in the manufacture of vascular grafts are highly conducive to this type of application. In other embodiments, metal ribbon or wire may be used and woven. Each of these filament materials has well-controlled surface and geometric properties, may be mass produced, and have a long history of implant use. In certain embodiments, the filaments may be "texturized" to provide rough surfaces and "hand-holds" onto which cell projections may attach. The filaments may be coated with extracellular matrix molecules or surface-treated (e.g. plasma irradiation) to enhance cellular adhesion to the filaments.

In one embodiment, the filaments, preferably organized in a non-random unidirectional orientation, are twisted in bundles to form yarns of varying thickness and void volume. Void volume is defined as the spaces existing between filaments. The void volume in the yarn should vary between 20–95%, but is preferably between 50–95%. The preferred void space between the filaments is between 20–200 $\mu$m, sufficient to allow the scaffold to be seeded with cells along the length of the yarn, and to allow the cells to attach to the filaments. The preferred diameter of the filaments comprising the yarn is between 5–100 $\mu$m. These filaments should have sufficient mechanical strength to allow twisting into a bundle to comprise a yarn. The filament cross-sectional shape can vary, with circular, rectangular, elliptical, triangular, and star-shaped cross-section being preferred.

In another embodiment, the filaments or yarns are woven into a mesh. The mesh can be produced on a braider using carriers, similar to bobbins, containing monofilaments or multifilaments, which serve to feed either the yarn or filaments into the mesh during weaving. The number of carriers is adjustable and may be wound with the same filaments or a combination of filaments with different compositions and structures. The angle of the braid, defined by the pick count, is controlled by the rotational speed of the carriers and the production speed. In one embodiment, a mandrel is used to produce a hollow tube of mesh. In certain embodiments, the braid is constructed as a single layer, in other embodiments it is a multi-layered structure. The tensile strength of the braid is the linear summation of the tensile strengths of the individual filaments.

Figure 2:
FIG. 2 is a depiction of PET yarn in non-woven strands.
Figure 3:
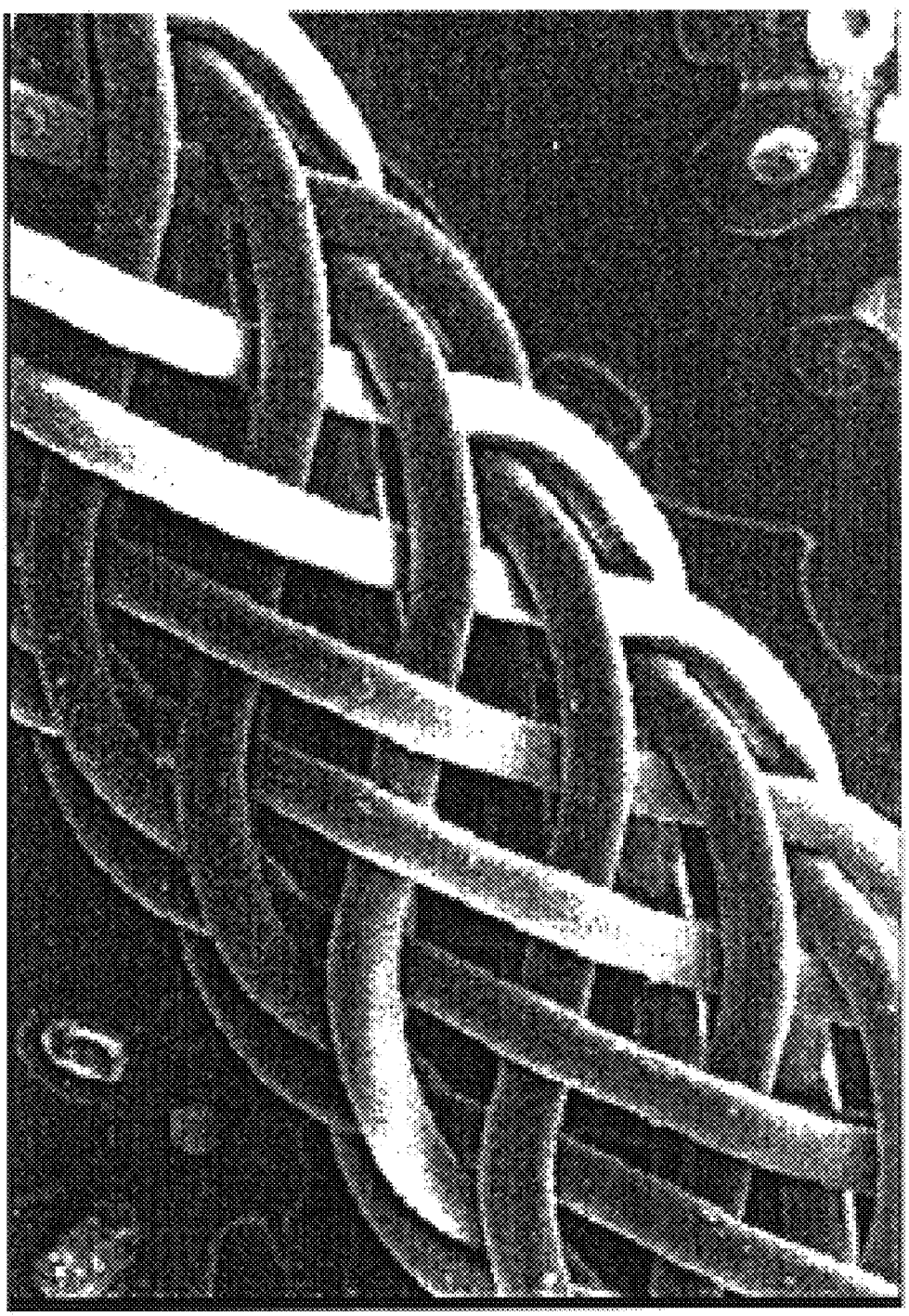
FIG. 3 is a depiction of nylon monofilaments woven into a braid.
Figure 4:
FIG. 4 is a depiction of nylon multifilaments woven into a braid.
Figure 5:
FIG. 5 is a depiction of stainless steel multifilaments woven into a mesh.

FIGS. 1–5 illustrate various configurations of the monofilaments used in the present invention. FIG. 1 illustrates PET yarn which is woven into a braid. The device has been stained with MTT black, which stains viable cells but does not stain non-viable cells. The PET braid in FIG. 1 was constructed from a 34 strand, 44 denier multifilament yarn woven onto a 760 $\mu$m O.D. mandrel with a 16 carrier braider at a pick count of 20 picks per inch (ppi). FIG. 2 shows PET yarn in non-woven strands. FIG. 3 illustrates nylon monofilaments woven into a braid. FIG. 4 illustrates nylon multifilaments woven into a braid. The nylon braid in FIG. 4 was constructed from a 13 strand, 40 denier multifilament yarn woven onto a 760 μm O.D. mandrel with a 16 carrier braider at a pick count of 18 ppi. FIG. 5 illustrates stainless steel multifilaments woven into a braid. The stainless steel braid in FIG. 5 was constructed from a ribbon woven onto a 900 μm O.D. mandrel with a 16 carrier braider at a pick count of 90 ppi. The tensile strength of PET, nylon, and stainless steel braids is 2.7, 2.4, and 3.6 kg force at break, respectively.

In one embodiment, a tubular braid is constructed. In an additional embodiment, the braid is inserted into a hollow fiber membrane. In a further embodiment, cells are seeded onto the hollow fiber membrane. In an additional embodiment, the cells are allowed to infiltrate the wall of the mesh tube to maximize the surface area available for cell attachment. In this embodiment, the braid serves both as a cell scaffold matrix and as an inner support for the device. The increase in tensile strength for the braid-supported device is significantly higher than in alternative approaches.

Cells

Many different cell types may be encapsulated in the device disclosed by the present invention. These include well known, publicly available immortalized cell lines as well as dividing primary cell cultures. Examples of suitable cell lines include Chinese hamster ovary cells (CHO); baby hamster kidney cells (BHK); mouse fibroblast-3T3 cells; African green monkey cell lines (including COS-1, COS-7, BSC-1, BSC-40, BMT-10 and Vero); rat adrenal pheochromocytoma (PC12 and PC12A); AT3, rat glial tumor (C6); EGF-responsive neurospheres; bFGF-responsive neural progenitor stem cells derived from the CNS of mammals [Richards et al., *PNAS* 89: 8591–8595 (1992); Ray et al., *PNAS* 90: 3602–3606 (1993)]; primary fibroblasts; Schwann cells; astrocytes; β-TC cells,;Hep-G2 cells; oligodendrocytes and their precursors; mouse myoblast cells-C2C12; human glial-derived cells-Hs683; human glial-derived cells-A172; porcine glioblasts; chondroblasts isolated from human long bone; rabbit corneal-derived cells (SIRC), and CAC cells.

In a preferred embodiment, the encapsulated cells are transfected with recombinant DNA molecules comprising DNA sequences coding for biologically active molecules operatively linked to promoters that are not subject to down regulation in vivo upon implantation into a mammalian host. Such methods of using encapsulated cells for the delivery of biologically active molecules is disclosed in U.S. Pat. No. 5,653,975, herein incorporated by reference. Methods for the use of encapsulated cells to deliver biologically active moieties and to provide metabolic functions (such as removal of harmful substances) have been disclosed in the art. See, e.g., U.S. Pat. No. 5,800,828, herein incorporated by reference.

Methods for controlling cell distribution within an encapsulation device have also been discussed. See, e.g., U.S. Pat. No. 5,795,790, herein incorporated by reference. The cells are exposed to a treatment that inhibits cell proliferation, promotes cell differentiation, or affects cell attachment to a growth surface within the bioartificial organ. Such treatments include the steps of (1) genetically manipulating cells, (2) exposing the cells to a proliferation-inhibiting compound or a differentiation-inducing compound or removing the cells from exposure to a proliferation-stimulating compound or a differentiation-inhibiting compound; exposing the cells to irradiation, and (3) modifying a growth surface of the encapsulation device with extracellular matrix molecules, molecules affecting cell proliferation or adhesion, or an inert scaffold, or a combination thereof. These treatments may be used in combination. In a preferred treatment, cells are exposed to and then removed from exposure to a proliferation-stimulating and differentiation inhibiting compound prior to encapsulation of the cells in the semipermeable biocompatible membrane. Upon in vivo implantation of the encapsulation device in a host, cellular proliferation is inhibited and cellular differentiation is promoted.

The methods described above provide for the long-term, stable, and efficacious delivery of biologically active molecules from living cells or provision of a metabolic or immunologic function to specific sites within a given mammal. The biologically active molecules contemplated include neurotransmitters, hormones, cytokines, lymphokines, enzymes, biological response modifiers, growth factors, and trophic factors.

The invention also contemplates encapsulation of two or more separately transfected cells or cell lines in the same device, each cell line secreting at least one of the desired molecules. Alternatively, separate devices producing each molecule separately may be implanted.

The invention further contemplates the use of different cell types during the course of the treatment regime. For example, a patient may be implanted with a capsule device containing a first cell type (e.g., BHK cells). If the patient subsequently develops an immune response to that cell type, the capsule can be retrieved, or explanted, and a second capsule can be implanted containing a second cell type (e.g., C2C12 cells). Thus, continuous provision of therapeutic molecules is possible.

Encapsulating Membrane

Encapsulation provides a protective barrier that hinders elements of the host immune system from destroying the cells. This allows the use of unmatched human or even animal tissue, without immunosuppression of the recipient and therefore results in an increase in the diversity of cell types that can be employed in therapy. Additionally, because the implanted cells are retained by a membrane, encapsulation of the cells prevents the inherent risk of tumor formation otherwise present in some cell-based treatments.

A "biocompatible capsule" is a capsule that, upon implantation in a host mammal, does not elicit a detrimental host response sufficient to result in the rejection of the capsule or to render it inoperable, such as through degradation. Numerous different encapsulation devices suitable for delivery of molecules are known. They may vary with respect to outer surface morphologies or other mechanical and structural characteristics. Preferably the capsule of this invention will be similar to those described in Aebischer et al., U.S. Pat. No. 5,800,828, herein incorporated by reference.

Useful biocompatible polymer capsules comprise (a) a core which contains tissue or cells, and (b) a surrounding or peripheral region of biocompatible, permselective membrane (jacket) which does not contain isolated cells (i.e., the membrane itself not immobilizing cells).

The "semi-permeable" nature of the capsule membrane permits molecules produced by the cells (metabolites, nutrients and therapeutic substances) to diffuse from the capsule into the surrounding host tissue, but is sufficiently impermeable to protect the cells in the core from detrimental immunological attack by the host.

Various polymers and polymer blends can be used to manufacture the capsule jacket, including, but not limited to, polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), PTFE, as well as derivatives, copolymers and mixtures of the foregoing.

Biocompatible semi-permeable hollow fiber membranes, and methods of making them are disclosed in U.S. Pat. Nos. 5,284,761 and 5,158,881 (see also, WO 95/05452), each incorporated herein by reference. In one embodiment, the capsule jacket is formed from a polyether sulfone hollow fiber, such as those described in U.S. Pat. Nos. 4,976,859 and 4,968,733, each incorporated herein by reference.

The tissue or cells in the core of the device may additionally be immobilized on an immobilizing matrix, such as a hydrogel or extracellular matrix components. In addition, the core of the device may contain an insert to create a "cell free" zone in the center of the core, so as to further reduce the possibility of a necrotic core of cells in the center of the device.

In a preferred embodiment, the capsules are immunoisolatory. An "immunoisolatory" capsule, upon implantation into a mammalian host, minimizes the deleterious effects of the host's immune system on the cells within the core of the capsule. To be immunoisolatory, the surrounding or peripheral region of the capsule should (a) confer protection to encapsulated cells from the immune system of the host in whom the capsule is implanted, (b) prevent harmful substances of the host's body from entering the core of the capsule, and (c) provide a physical barrier sufficient to prevent detrimental immunological contact between the isolated cells and the immune system of the host. The thickness of this physical barrier can vary, but it will always be sufficiently thick to prevent direct contact between the cells and/or substances on either side of the barrier. The thickness of this region generally ranges between 5 and 200 microns; a thickness of 10 to 100 microns is preferred, and thickness of 20 to 75 microns is particularly preferred. Types of immunological attack which can be prevented or minimized by the use of the instant vehicle include, but are not limited to, attack by macrophages, neutrophils, cellular immune responses (e.g., natural killer cells and antibody-dependent T cell-mediated cytolysis (ADCC)), and humoral response (e.g., antibody-dependent, complement-mediated cytolysis).

An immunoisolotory capsule can be used for the delivery of products having a wide range of molecular sizes. Accordingly, nominal molecular weight cutoff (MWCO) values from 50 kilodaltons (kDa) up to 1000–2000 kDa are contemplated by this invention. In preferred embodiments, the molecular weight cutoff is between 50–700 kDa. In particularly preferred embodiments, the molecular weight cutoff is between 70–300 kDa.

The capsule can have any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved at some time after it is implanted, configurations which tend to lead to migration of the capsules from the site of implantation (such as spherical capsules small enough to travel in the recipient's blood vessels) should be avoided. Preferred embodiments of this invention include shapes that offer high structural integrity and are easy to retrieve from the host. Such shapes include rectangular patches, disks, cylinders, and flat sheets.

In one embodiment, the implantable capsule is of a sufficient size and durability for complete retrieval after implantation, and preferably the device has a tether that aids in retrieval. Such tethers are well known in the art. Macrocapsules can be fabricated to have a volume in excess of 100 $\mu$l for some embodiments. These macrocapsules have a core preferably having a minimum volume of about 1 to 10 $\mu$l.

Cell loading density may be varied over a wide range. We contemplate encapsulation of between $10^4$ to $10^9$, preferably $10^5$ to $10^7$ cells, in each device. The monofilaments, yarn, or mesh may be inserted in a hollow membrane tube. Cells, either in aqueous solution or in a hydrogel, are then injected into the membrane and the ends of the device are sealed.

Any suitable method of sealing the capsules may be used. Preferred methods of sealing include the employment of polymer adhesives, crimping, knotting and heat sealing. These sealing techniques are known in the art. In other preferred embodiments, any suitable "dry" sealing method is used, as described in U.S. Pat. No. 5,738,673, incorporated herein by reference. In such methods, a substantially non-porous fitting is provided through which the cell-containing solution is introduced. Subsequent to filling, the capsule is sealed. Methods of sealing the capsules are known in the art.

The methods and devices of this invention are intended for use in a mammalian host, recipient, patient, subject or individual, preferably a primate, most preferably a human.

A number of different implantation sites are contemplated for the devices and methods of this invention. These implantation sites include systemic implantation, including subcutaneous, intravenous, or intramuscular implantation, and implantation into the central nervous system, including the brain, spinal cord, and aqueous and vitreous humors of the eye, intrathecally, and into the lateral ventricles.

The actual dosage can be varied by any suitable method known in the art, including, e.g., by implanting a fewer or greater number of capsules. For macrocapsular delivery, we prefer between one and ten capsules.

The following examples are presented in order to more fully illustrate the preferred embodiments of the invention. These examples should in no way be construed as limiting the scope of the invention, as defined by the appended claims.

EXAMPLE 1

Porcine Glial-Derived Cells Encapsulated Within Hollow Fiber Membranes with a Pet Yarn Scaffold Devices having internal PET yarn scaffolds were compared with prior art devices having a hydrogel matrix core or foam matrix core. The following devices were prepared (n=10/group, n=40, total):

(1) PET yarn coated with laminin;
(2) PVA foam coated with laminin;
(3) Vitrogen® (collagen hydrogel);
(4) Matrigel® (ECM from mouse sarcoma);

The porcine glial-derived cell line was immortalized with the MX-1 gene (str1, MX-1, lipid 6) (substantially as described in, e.g., WO 96/02646). The hollow fiber membrane for these experiments was a polyethersulfone hollow fiber (Akzo Nobel) with an ID -870 μm and an O.D. of 1.1 mm. The devices containing the hydrogel matrices were prepared by mixing the cells 1:1 with the liquid hydrogel solution (either Matrigel® or Vitrogen®). The hydrogel/cell slurry was then injected into the hollow fiber membranes. For the PET and PVA foam matrices, the cells were injected into the hollow fiber membranes that had been pre-manufactured with the PET and PVA foam within the lumen. For all devices, the final number of cells was 200,000/device. Devices were held in vitro for 2 weeks in a 37° C., humidified incubator. Cell medium was replenished 3×/week.

Figure 6:
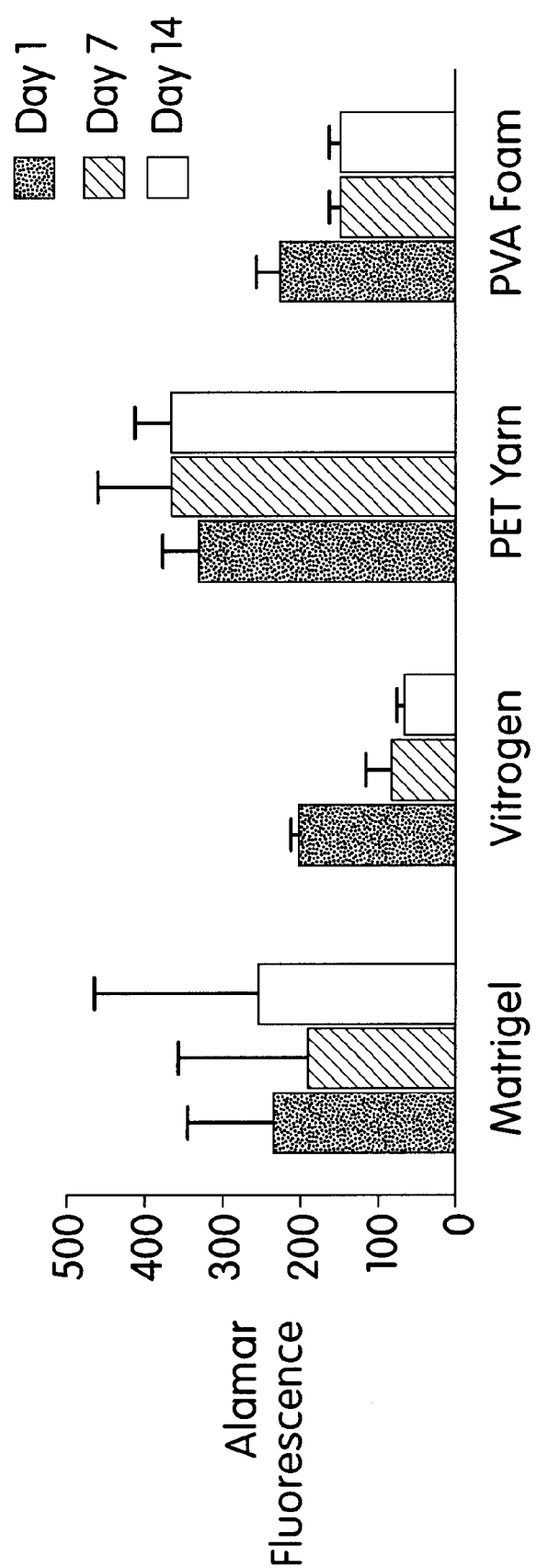
FIG. 6 is graph of Alamar fluorescence data for the present invention as compared to prior art devices.

Cell growth rate was monitored weekly with the Alamar Blue assay. This assay is a quantitative measurement of the proliferation of human and animal cell lines which incorporates a fluorimetric/colorimetric growth indicator to detect metabolic activity. In encapsulation devices, the Alamar signal typically correlates linearly with the number of cells in the device. The Alamar Blue data shown in FIG. 6 indicate that the number of healthy, viable cells in the PET yarn is significantly higher than with either Vitrogen® or PVA foam. The error bars for the matrix are large and overlap with the PET data, indicating that. However, the histology data shown in TABLE 1 indicate a significantly healthier cell morphology in the PET yarn matrix than with Matrigel®. Alamar fluorescence assays were performed at day one, day seven and day 14 post-encapsulation. Additionally, devices were randomly selected for histological sectioning at day seven and day 14 post-encapsulation and rated for confluence and viability.

A number of other cell types were encapsulated with PET yarn or PET mesh or nylon mesh and analyzed for survival using a similar protocol as above. The data are summarized in TABLE 2.

TABLE 2

| CELL TYPE | RATING |
|---|---|
| Hs683 -- a human glial-derived cell line | * |
| A172 -- a human glial-derived cell line | * |
| porcine glioblast | * |
| chondroblast -- isolated from human long bone | ** |
| 373 mouse fibroblasts | * |
| SIRC (rabbit corneal derived) | * |
| Chinese Hamster Ovary cells | ** |
| Baby Hamster Kidney Cells | ** |
| C2Cl2 mouse myoblast Cells | * |
| CAC cells | * |

Rating Key
*cell lines that had optimal survival with PET yarn or mesh matrix.
**cell lines that had good survival with PET yarn or mesh matrix with equivalent survival to other matrices tested but differing morphology.

These cell lines were also tested with at least two hydrogel naturally-derived matrices (either collagen, chitosan, alginate or agarose) and the PVA foam. Both Alamar fluorescence and histological viability determined that the best matrix for many these cell types was either the PET yarn or mesh. Viability for chondroblasts was equally high for both alginate matrix and PET yarn; however, the morphology of the cells in each matrix was dramatically different. In the PET yarn matrix, the cells de-differentiated into a proliferating fibroblastic morphology. In alginate, however, the chondroblasts remained rounded and differentiated—indicating that the substrate had a biological effect on the cells. Both the PET mesh and PET yarn matrices were superior than Vitrogen® and PVA foam in promoting encapsulated cell viability with 3T3 mouse fibroblast cells. There was not a significant difference between performance of the PET yarn and PET mesh. SIRC cells derived from rabbit cornea also showed significantly enhanced Alamar fluorescence signal and viability as assessed by FDA/PI for devices

TABLE 1

PORCINE GLIOBLAST HISTOLOGY DEVICE RATINGS

| DEVICE | RATING | % VIABILITY | COMMENTS |
|---|---|---|---|
| DAY 7 | | | |
| PET yarn | 6, 8 | 5 | 90+ | Confluent throughout center, fibroblastic morphology along yarn; patches of necrotic cells. |
| PVA foam | 17, 18 | 5 | 70 | Larger patches of necrotic cells. |
| Vitrogen ® | 27, 28 | 1.5 | 5 | Mostly pyknotic/dying cells. |
| Matrigel ® | 37 | 1 | 1 | Mostly pyknotic/dying cells. |
| DAY 14 | | | |
| PET yarn | 6, 8 | 5 | 90+ | Confluent throughout center, fibroblastic morphology along yarn; patches of necrotic cells. |
| PVA foam | 11,12,13,14 | 4 | 70 | Core of necrotic cells. |
| Vitrogen ® | 21, 22, 23 | 2 | 10 | Mostly pyknotic/dying cells. |
| Matrigel ® | 31, 32, 33 | 1 | 10–40 | Mostly pyknotic/dying cells. |

RATING KEY
0    no viable cells
1    pyknotic single cells, unhealthy but viable
2    sparse viable, healthy cells mixed with majority unhealthy cells
3    small–medium size mostly healthy/viable clusters or viable rims >3 cell layers
4    larger mostly viable clusters or rims of viable cells >50 μm w/necrotic core
5    no necrotic core, majority healthy cells throughout device with PET yarn (60+% viable for PET yarn matrix devices versus <5% viability for the collagen gel matrix). All cell lines listed in TABLE 2 had a morphology change once encapsulated with the PET yarn or mesh.

EXAMPLE 2

C2C12, BHK and CHO Cells Encapsulated within Hollow Fiber Membranes with Yarn or a Mesh Scaffold Implanted into Sheep C2C12 mouse myoblast cells secreting NT4/5 were encapsulated in devices and implanted into the sheep intrathecal space. Devices were retrieved after 1 month, assessed for viability, and assayed for growth factor output. Percentages of sheep with growth factor output in the cerebral spinal fluid (CSF) are listed in TABLE 3. PET yarn and PVA foam were tested in two types of hollow fiber membranes. The PET yarn performance was equivalent to that of the PVA foam in a PAN/PVC hollow fiber and significantly better than the PVA foam in a polyethersulfone ("PES") hollow fiber. Histology sections showed a significantly higher percentage of viable cells in the PES fiber with PET yarn than with the PVA foam.

TABLE 3

|  | % sheep with CSF levels of NT4/5 | % devices with levels of NT4/5 on explant |
|---|---|---|
| Cerecrib fiber |  |  |
| PET yarn | 66% | 100% |
| PVA foam | 100% | 66% |
| Akzo flber |  |  |
| PET yarn | 100% | 75% |
| PVA foam | 66% | 33% |

CHO cells encapsulated in similar devices implanted into sheep intrathecal space showed equivalent viability between devices with PVA and PET matrix.

EXAMPLE 3

Figure 7:
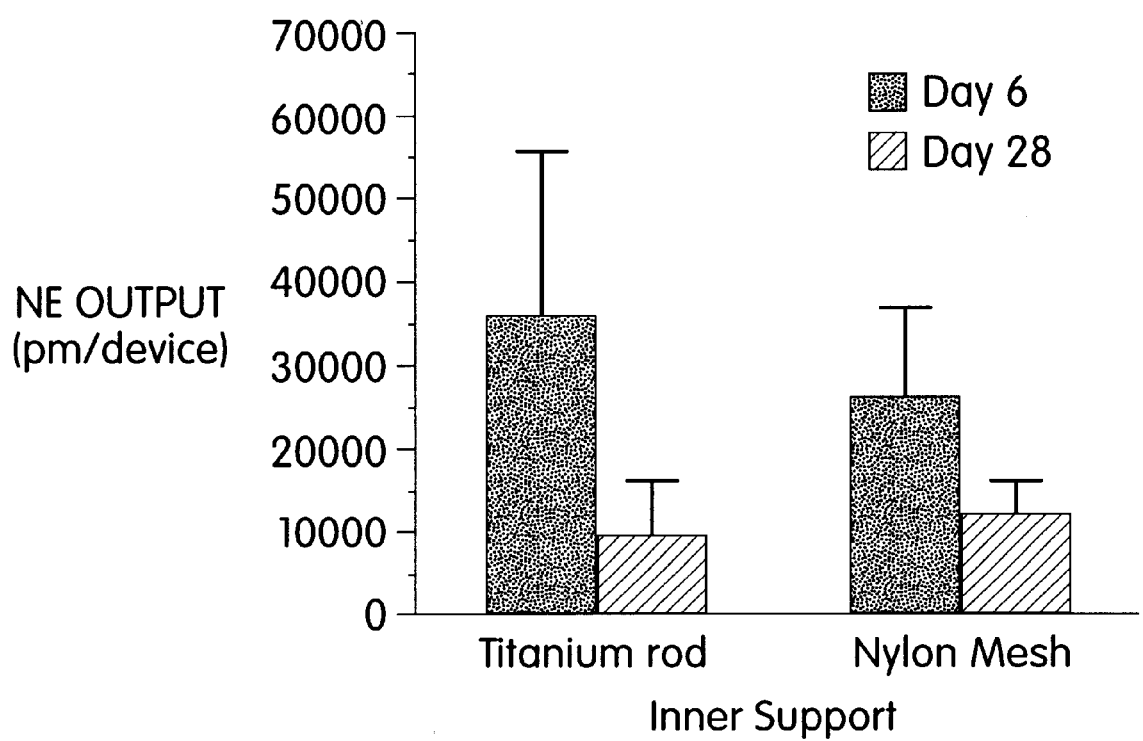
FIG. 7 is a graph of the basal NE output of a device with a titanium rod as an inner support with the output of a device having nylon mesh as inner support.

CAC Cells Encapsulated within Hollow Fiber Membranes Supported with a Nylon Braided Mesh Tape The performance of calf adrenal chromaffin cell devices containing a titanium rod as an inner support was compared to that of CAC devices containing nylon braided mesh as an inner support (n=4). All other device components were identical. The basal norepinephrine (NE) output was measured at day 6 and day 28, the lysate dopamine (DA) output was measured at day 28, and the cell viability and distribution were qualitatively determined with FDA/PI staining of the noodle at day 28. The output performance between the two device configurations was identical, as is shown in FIG. 7. FDA/PI evaluation of the extruded noodles at day 28 showed no difference between loading distribution, loading density, and cell viability between the two configurations.

Those of skill in the art will recognize that the invention may be embodied in other specific forms without departing from the spirit or essential characteristics thereof. The presently described embodiments are presented by way of example only and are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein

We claim:

1. A device containing encapsulated cells or tissue for implanting into a host comprising:
   (a) a substantially non-degradable filamentous cell-supporting matrix, wherein the matrix comprises a plurality of monofilaments, and wherein said monofilaments are twisted into a yarn or woven into a mesh, and the cells or tissue are distributed thereon; and
   (b) a semi-permeable encapsulating membrane surrounding the matrix.

2. The device of claim 1, wherein the filamentous cell-supporting matrix comprises a biocompatible material selected from the group consisting of acrylic, polyester, polyethylene, polypropylene polyacetonitrile, polyethylene terephthalate, nylon, polyamides, polyurethanes, polybutester, silk, cotton, chitin, carbon, and biocompatible metals.

3. The device of claim 1, wherein the filamentous cell-supporting matrix is a yarn.

4. The device of claim 1, wherein the filamentous cell-supporting matrix is a mesh.

5. The device of claim 1, wherein the matrix forms a cylinder.

6. The device of claim 1, wherein the cells or tissue produce a bilogically active molecule selected from the group consisting of neurotransmitters, hormones, cytokines, lymphokines, enzymes, growth factors, and trophic factors.

7. A method of making an implantation device containing encapsulated cells or tissue comprising the steps of:
   (a) providing a substantially non-degradable filamentous cell supporting matrix, wherein the matrix comprises a plurality of monofilaments, and wherein said monofilaments are twisted into a yarn or woven into a mesh;
   (b) inserting the matrix into a capsule formed of a semi-permeable membrane through an opening in the capsule;
   (c) distributing cells or tissue onto the matrix through the opening of the capsule; and
   (d) sealing the opening of the capsule.

8. The method of claim 7, wherein the filamentous cell-supporting matrix is a yarn.

9. The method of claim 7, wherein the filamentous cell-supporting matrix is a mesh.

10. The method of claim 7, wherein the matrix forms a cylinder.

11. The method of claim 7, wherein the matrix is coated with extracellular matrix molecules.

12. The method of claim 7, wherein the cells or tissue produce a biologically active molecule selected from the group consisting of neurotransmitters, hormones, cytokines, lymphokines, enzymes, growth factors, and trophic factors.

* * * * *